(12) United States Patent
Vaysse-Ludot et al.

(10) Patent No.: US 7,091,364 B2
(45) Date of Patent: Aug. 15, 2006

(54) PROCESS FOR THE INDUSTRIAL SYNTHESIS OF TETRAESTERS OF 5-[BIS(CARBOXYMETHYL)AMINO]-3-CARBOXYMETHYL-4-CYANO-2-THIOPHENECARBOXYLIC ACID, AND APPLICATION TO THE SYNTHESIS OF BIVALENT SALTS OF RANELIC ACID AND THEIR HYDRATES

(75) Inventors: Lucile Vaysse-Ludot, Saint-Wandrille-Rancon (FR); Jean-Pierre Lecouve, Le Havre (FR); Pascal Langlois, Saint-Jean de la Neuville (FR)

(73) Assignee: Les Laboratoires Servier, Courbevoie (FR)

( * ) Notice: Subject to any disclaimer, the term of this patent is extended or adjusted under 35 U.S.C. 154(b) by 218 days.

(21) Appl. No.: 10/669,302

(22) Filed: Sep. 24, 2003

(65) Prior Publication Data

US 2004/0059134 A1    Mar. 25, 2004

(30) Foreign Application Priority Data

Sep. 24, 2002    (FR) .................................. 02 11765

(51) Int. Cl.
*C07D 333/38* (2006.01)

(52) U.S. Cl. ........................................................ 549/61
(58) Field of Classification Search ................... 549/61
See application file for complete search history.

(56) References Cited

U.S. PATENT DOCUMENTS 5,128,367 A    7/1992  Wierzbicki et al.
5,153,330 A *  10/1992 Barker et al. .................. 549/61
5,747,578 A *  5/1998  Schmitz et al. .............. 524/502
6,686,478 B1 * 2/2004  Muller et al. .................. 549/61
6,835,745 B1 * 12/2004 Coghlan et al. ............ 514/448

FOREIGN PATENT DOCUMENTS

EP    0253259    1/1988
EP    0415850    3/1991
EP    0813869    12/1997

OTHER PUBLICATIONS

*Eurasian Search Report for Eurasian Application No. 200300927*, Dec. 18, 2003.
*International Search Report for International No. PCT/FR 03/02775*, Feb. 2, 2004.
Wierzbicki, et al., *Bull. Chim. Soc. Fr.*, 1975, 7-8, 1786-1792.

* cited by examiner

*Primary Examiner*—Deborah C. Lambkin
(74) *Attorney, Agent, or Firm*—Hueschen and Sage

(57) ABSTRACT

The process for the industrial synthesis of compounds of formula (I):

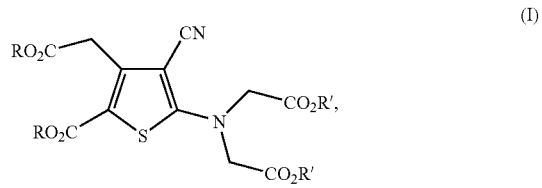

wherein R and R', which are the same or different, each represent linear or branched $(C_1–C_6)$alkyl.

Application to the synthesis of bivalent salts of ranelic acid and more especially strontium ranelate and its hydrates.

12 Claims, No Drawings

PROCESS FOR THE INDUSTRIAL SYNTHESIS OF TETRAESTERS OF 5-[BIS(CARBOXYMETHYL)AMINO]-3-CARBOXYMETHYL-4-CYANO-2-THIOPHENECARBOXYLIC ACID, AND APPLICATION TO THE SYNTHESIS OF BIVALENT SALTS OF RANELIC ACID AND THEIR HYDRATES

The present invention relates to a process for the industrial synthesis of tetraesters of 5-[bis(carboxymethyl)amino]-3-carboxymethyl-4-cyano-2-thiophenecarboxylic acid and to the application thereof in the industrial production of bivalent salts of ranelic acid and their hydrates.

More specifically, the present invention relates to a new process for the industrial synthesis of compounds of formula (I):

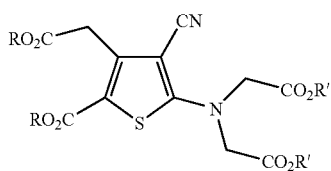
(I)

wherein R and R', which are the same or different, each represent a linear or branched $(C_1-C_6)$alkyl group.

The compounds of formula (I) obtained according to the process of the invention are useful in the synthesis of ranelic acid, its strontium, calcium or magnesium salts of formula (II):

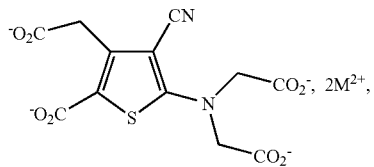
(II)

wherein M represents strontium, calcium or magnesium, and hydrates of the said salts.

BACKGROUND OF THE INVENTION

The bivalent salts of ranelic acid have very valuable pharmacological and therapeutic properties, especially pronounced anti-osteoporotic properties, making these compounds useful in the treatment of bone diseases.

DESCRIPTION OF THE PRIOR ART

The bivalent salts of ranelic acid, and more especially strontium ranelate, the preparation thereof and the therapeutic use thereof have been described in the European Patent Specification EP 0 415 850.

In view of the pharmacological interest of that compound, it has been important to be able to synthesise the intermediate of formula (I) by using an effective industrial synthesis process, allowing the compound of formula (I) to be obtained in a good yield and with excellent purity, but which is also readily transferable to the industrial scale.

The journal Bull. Soc. Chim. France 1975, pp. 1786–1792, describes obtaining a compound of formula (I) (R=R'=ethyl) by reacting 5-amino-3-(carboxymethyl)-4-cyano-2-thiophenecarboxylic acid with ethyl bromoacetate, in the presence of potassium carbonate, followed by isolation in a highly dilute aqueous-organic medium.

However, the low yield of that reaction (65%), the large amount of aqueous saline waste generated by that reaction and, above all, the very long reaction time (5 days) have completely precluded use of that reaction on an industrial scale.

The Applicant has now developed a simple industrial synthesis process which allows the compound of formula (I) to be obtained in a very good yield, with a considerably shorter reaction time and excellent purity and in which the aqueous saline waste is completely avoided.

DETAILED DESCRIPTION OF THE INVENTION

More specifically, the present invention relates to a process for the industrial synthesis of compounds of formula (I), which process is characterised in that a compound of formula (III):

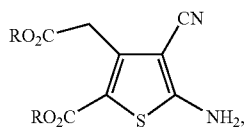
(III)

wherein R represents a linear or branched $(C_1-C_6)$alkyl group,
is reacted with a compound of formula (IV):

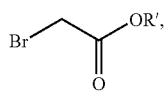
(IV)

wherein R' represents a linear or branched $(C_1-C_6)$alkyl group,
in the presence of a catalytic amount of a $C_8-C_{10}$-type quaternary ammonium compound,
and in the presence of potassium carbonate,
at the reflux of an organic solvent;
the reaction mixture is subsequently filtered;
the mixture is then concentrated by distillation;
a co-solvent is then added,
and the reaction mixture is cooled and filtered
to yield, after drying of the powder thereby obtained, the compound of formula (I).

A $C_8-C_{10}$-type quaternary ammonium compound is understood to be a compound of formula (A) or a mixture of compounds of formula (A):

$$R_1R_2R_3R_4-N^+X^-\qquad(A)$$

wherein $R_1$ represents a $(C_1-C_6)$alkyl group, $R_2$, $R_3$ and $R_4$, which are the same or different, each represent a $(C_8-C_{10})$ alkyl group, and X represents a halogen atom. $C_8-C_{10}$-type quaternary ammonium compounds to which preference is given are the catalysts Adogen 464® and Aliquat 336®.

Surprisingly, only the use of a $C_8$–$C_{10}$-type quaternary ammonium compound allows the compound of formula (I) to be obtained both with a greatly reduced reaction time and with very good selectivity, in contrast to other types of quaternary ammoniums, as the following Table shows:

| Catalyst | Duration of reaction | Content of reaction mixture |
| --- | --- | --- |
| Tetrabutylammonium hydrogen sulphate (TBAHS) | 12 hours | 92% |
| N,N-bis(2-hydroxyethyl)-N-methyl 1-dodecanaminium bromide | 18 hours | 82% |
| Adogen 464 ® | 5 hours | 96% |
| Aliquat 336 ® | 4 hours | 95% |

Furthermore, the somewhat simplified isolation (the precipitation step followed by filtration has been replaced by simple filtration of the reaction mixture) allows, by virtue of the particular conditions developed, the compound of formula (I) to be obtained not only in a very good yield (89%) but also with excellent purity (greater than 98%), whilst avoiding the burden on the environment that the aqueous saline waste represented.

The amount of potassium carbonate is preferably from 2 to 3 mol per mol of compound of formula (III).

The amount of compound of formula (IV) is preferably from 2 to 3 mol per mol of compound of formula (III).

The initial volume of organic solvent is preferably from 6 to 12 ml per gram of compound of formula (III).

Organic solvents that are preferred for the reaction are acetone and acetonitrile.

A co-solvent that is preferred for isolation is methanol.

Methyl 5-[bis(2-methoxy-2-oxoethyl)amino]-4-cyano-3-(2-methoxy-2-oxoethyl)-2-thiophenecarboxylate and methyl 5-[bis(2-ethoxy-2-oxoethyl)amino]-4-cyano-3-(2-methoxy-2-oxoethyl)-2-thiophenecarboxylate, particular and preferred cases of the compounds of formula (I), are new compounds which are useful as synthesis intermediates in the chemical or pharmaceutical industry, especially in the synthesis of strontium ranelate and accordingly form an integral part of the present invention.

The Examples hereinbelow illustrate the invention but do not limit it in any way.

EXAMPLE 1

Methyl 5-[bis(2-methoxy-2-oxoethyl)amino]-4-cyano-3-(2-methoxy-2-oxoethyl)-2-thiophenecarboxylate Introduce into a reactor 400 kg of 5-amino-3-(carboxymethyl)-4-cyano-2-thiophenecarboxylic acid, 478 kg of potassium carbonate, 2810 litres of acetone, 16 kg of Adogen 464® and 529.6 kg of methyl bromoacetate.

Bring the temperature to 60° C. After refluxing for 5 hours, cool the reaction mixture and then filter it. Concentrate the filtrate obtained.

Add methanol; cool and filter the suspension obtained, and then dry the powder.

Methyl 5-[bis(2-methoxy-2-oxoethyl)amino]-4-cyano-3-(2-methoxy-2-oxoethyl)-2-thiophenecarboxylate is thereby obtained in a yield greater than 85% and with a chemical purity greater than 98%.

EXAMPLE 2

Methyl 5-[bis(2-methoxy-2-oxoethyl)amino]-4-cyano-3-(2-methoxy-2-oxoethyl)-2-thiophenecarboxylate Methyl 5-[bis(2-methoxy-2-oxoethyl)amino]-4-cyano-3-(2-methoxy-2-oxoethyl)-2-thiophenecarboxylate is obtained in the same manner as Example 1, but replacing Adogen 464® by Aliquat 336®.

EXAMPLE 3

Methyl 5-[bis(2-methoxy-2-oxoethyl)amino]-4-cyano-3-(2-methoxy-2-oxoethyl)-2-thiophenecarboxylate Methyl 5-[bis(2-methoxy-2-oxoethyl)amino]-4-cyano-3-(2-methoxy-2-oxoethyl)-2-thiophenecarboxylate is obtained in the same manner as Example 1, but replacing the acetone by acetonitrile.

EXAMPLE 4

Methyl 5-[bis(2-ethoxy-2-oxoethyl)amino]-4-cyano-3-(2-methoxy-2-oxoethyl)-2-thiophenecarboxylate Methyl 5-[bis(2-ethoxy-2-oxoethyl)amino]-4-cyano-3-(2-methoxy-2-oxoethyl)-2-thiophenecarboxylate is obtained in the same manner as Example 1, but replacing the 529.6 kg of methyl bromoacetate by 578.1 kg of ethyl bromoacetate.

We claim:

1. A process for the industrial synthesis of a compound of formula (I):

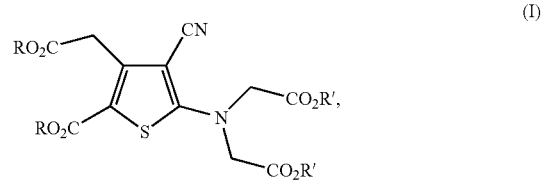

wherein R and R', which are the same or different, each represent linear or branched ($C_1$–$C_6$)alkyl, wherein a compound of formula (III):

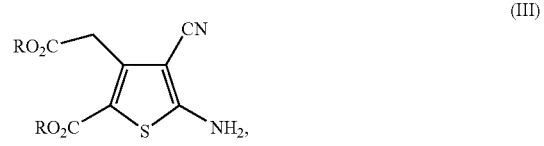

wherein R is as defined hereinbefore, is reacted with a compound of formula (IV):

wherein R' is as defined hereinbefore, in the presence of a catalytic amount of a $C_8$–$C_{10}$-type quaternary ammonium compound, and in the presence of potassium carbonate, at reflux with an organic solvent;

the reaction mixture is subsequently filtered;

the mixture is then concentrated by distillation;

a co-solvent is then added, and the reaction mixture is cooled and filtered to yield, after drying of the powder thereby obtained, the compound of formula (I), it being understood that a $C_8$–$C_{10}$-type quaternary ammonium compound is a compound of formula (A) or a mixture of compounds of formula (A):

$$R_1R_2R_3R_4\text{–}N^+\text{–}X \qquad (A)$$

wherein $R_1$ represents $(C_1$–$C_6)$alkyl, $R_2$, $R_3$ and $R_4$, which are identical or different, each represent $(C_8$–$C_{10})$alkyl, and X represents halogen.

2. The synthesis process of claim 1 allowing the compound of formula (I), wherein R represents a methyl group and R' represents an ethyl group, to be obtained.

3. The synthesis process of claim 1 allowing the compound of formula (I), wherein R and R' each represent a methyl group, to be obtained.

4. The synthesis process of claim 1, wherein the $C_8$–$C_{10}$-type quaternary ammonium compound is a mixture of methyl trioctylammonium chloride, of methyl trinonylammonium chloride and of methyl tridecylammonium chloride or a mixture of methyl tri-n-octylammonium chloride and methyl tridecylammonium chloride with methyl tri-n-octylammonium chloride predominating.

5. The synthesis process of claim 1, wherein the amount of potassium carbonate is from 2 to 3 mol per mol of compound of formula (III).

6. The synthesis process of claim 1, wherein the amount of compound of formula (IV) is from 2 to 3 mol per mol of compound of formula (III).

7. The synthesis process of claim 1, wherein the initial volume of organic solvent is from 6 to 12 ml per gram of compound of formula (III).

8. The synthesis process of claim 1, wherein the organic solvent used for the reaction is acetone or acetonitrile.

9. The synthesis process of claim 1, wherein the co-solvent used during isolation is methanol.

10. The synthesis process of claim 1, wherein the compound of formula (I) obtained has a chemical purity greater than 98%.

11. The process for the synthesis of ranelic acid, its strontium, calcium or magnesium salts and hydrates of the said salts, starting from a compound of formula (I):

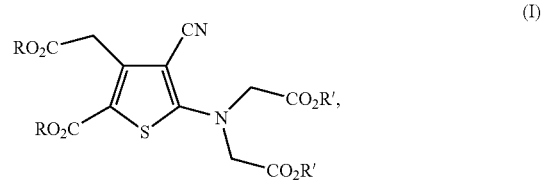

wherein R and R', which are the same or different, each represent linear or branched $(C_1$–$C_6)$alkyl, wherein the compound of formula (I) is obtained by the synthesis process of claim 1.

12. The process for the synthesis of strontium ranelate and its hydrates, starting from a compound of formula (I):

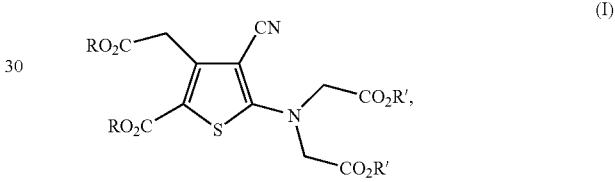

wherein R and R', which are the same or different, each represent linear or branched $(C_1$–$C_6)$alkyl, wherein the compound of formula (I) is obtained by the synthesis process of claim 1.

* * * * *

UNITED STATES PATENT AND TRADEMARK OFFICE
CERTIFICATE OF CORRECTION

| | |
|---|---|
| PATENT NO. | : 7,091,364 B2 |
| APPLICATION NO. | : 10/669302 |
| DATED | : August 15, 2006 |
| INVENTOR(S) | : Lucile Vaysse-Ludot et al. |

It is certified that error appears in the above-identified patent and that said Letters Patent is hereby corrected as shown below:

Column 3, Line 54: "400 kg of" should be --400 kg of the dimethyl ester of--.

Signed and Sealed this

Seventh Day of August, 2007

JON W. DUDAS
*Director of the United States Patent and Trademark Office*